US012584115B2

(12) United States Patent
Hoying et al.

(10) Patent No.: US 12,584,115 B2
(45) Date of Patent: Mar. 24, 2026

(54) MODELS AND METHODS TO ESTABLISH PERFUSABLE, COMPARTMENTALIZED, LYMPHOID TISSUE MODELS IN THREE-DIMENSIONAL IN VITRO CULTURE

(71) Applicant: Advanced Solutions Life Sciences, LLC, Louisville, KY (US)

(72) Inventors: James B. Hoying, Manchester, NH (US); Hannah A. Strobel, Manchester, NH (US); Sarah Moss, Manchester, NH (US)

(73) Assignee: ADVANCED SOLUTIONS LIFE SCIENCES, LLC, Louisville, KY (US)

( * ) Notice: Subject to any disclaimer, the term of this patent is extended or adjusted under 35 U.S.C. 154(b) by 740 days.

(21) Appl. No.: 17/979,209

(22) Filed: Nov. 2, 2022

(65) Prior Publication Data

US 2023/0138186 A1 May 4, 2023

Related U.S. Application Data

(60) Provisional application No. 63/274,647, filed on Nov. 2, 2021.

(51) Int. Cl.
| | |
|---|---|
| *C12N 5/071* | (2010.01) |
| *C12M 1/00* | (2006.01) |

(Continued)

(52) U.S. Cl.
CPC ........... *C12N 5/0697* (2013.01); *C12M 23/16* (2013.01); *C12M 29/10* (2013.01); *C12N 5/0635* (2013.01);

(Continued)

(58) Field of Classification Search
CPC ....... B29C 64/106; B33Y 10/00; B33Y 80/00; C12M 21/08; C12M 23/16; C12M 25/14;

(Continued)

(56) References Cited

U.S. PATENT DOCUMENTS

| | | | | |
|---|---|---|---|---|
| 2005/0282148 | A1* | 12/2005 | Warren | ................ C12N 5/0698 |
| | | | | 435/366 |
| 2022/0106547 | A1* | 4/2022 | Petropolis | ............ C12N 5/0688 |

FOREIGN PATENT DOCUMENTS

| | | | |
|---|---|---|---|
| WO | 2014100456 | A1 | 6/2014 |
| WO | 2016179242 | A1 | 11/2016 |

(Continued)

OTHER PUBLICATIONS

International Search Report and Written Opinion dated Feb. 16, 2023 pertaining to PCT International application No. PCT/US2022/048675 filed Nov. 2, 2022, pp. 1-10.

(Continued)

*Primary Examiner* — Michael L Hobbs
(74) *Attorney, Agent, or Firm* — DINSMORE & SHOHL LLP

(57) ABSTRACT

A three-dimensional (3D) lymphoid tissue model is provided, the model including a cellularized stromal compartment and a plurality of cellularized compartments including lymphocytes disposed within the stromal compartment; and a controlled fluid perfusion system configured to perfuse the model with a perfusion fluid. Methods of fabricating a 3D lymphoid tissue model and producing antibodies with the 3D lymphoid tissue model are also provided.

21 Claims, 6 Drawing Sheets

(51) Int. Cl.

| | |
|---|---|
| *C12M 3/06* | (2006.01) |
| *C12N 5/0781* | (2010.01) |
| *C12N 5/0783* | (2010.01) |
| *C12P 21/00* | (2006.01) |

(52) U.S. Cl.
CPC ............ *C12N 5/0636* (2013.01); *C12P 21/00* (2013.01); *C12N 2513/00* (2013.01); *C12N 2533/90* (2013.01)

(58) Field of Classification Search
CPC .... C12M 29/10; C12N 5/0634; C12N 5/0635; C12N 5/0636; C12N 2500/25; C12N 2501/2321; C12N 2513/00; C12N 2533/30; C12N 2533/54; C12N 2533/90; C12N 2537/10; C12P 21/00; C12P 21/02
See application file for complete search history.

(56) References Cited

FOREIGN PATENT DOCUMENTS

| | | | | |
|---|---|---|---|---|
| WO | 2017100858 A1 | 6/2017 | | |
| WO | WO-2018017605 A1 * | 1/2018 | ................ | A61P 7/00 |

OTHER PUBLICATIONS

Polini, A. et al. "Towards the development of human immune-system-on-a-chip platforms" Drug Discovery Today, Feb. 2019, pp. 1-17.
Zheng, F. et al. "Organ-on-a-Chip Systems: Microengineering to Biomimic Living Systems" Small, Feb. 2016, pp. 1-31.

* cited by examiner

Perfusion setup

MODELS AND METHODS TO ESTABLISH PERFUSABLE, COMPARTMENTALIZED, LYMPHOID TISSUE MODELS IN THREE-DIMENSIONAL IN VITRO CULTURE

RELATED APPLICATIONS

This application claims the benefit of priority to U.S. Provisional Patent Application 63/274,647, filed Nov. 2, 2021, the content of which is hereby incorporated by reference in its entirety.

TECHNICAL FIELD

The present disclosure relates to the field of in vitro lymphatic tissue models. Specifically, this disclosure relates to in vitro compartmentalized lymphoid tissue models and their methods of manufacture and use.

BACKGROUND

A key feature of lymphoid tissue is compartmentalized, hematopoietic cells, including B cell-rich follicles and T cell-rich interior zones, and perfusion of the tissue with interstitial fluid. The lymphatic system includes a network of lymphatic vessels, lymphoid organs, lymphoid tissues, and circulating lymph and is characterized by complex immune cell dynamics. These features permit efficient and controlled primary and secondary immune reactions to antigens. Furthermore, dynamics between the circulatory system and the lymphatic system are critical to organization of lymphoid tissue architecture and adaptive immune response, including antibody production and transport of lymphocytes.

An in vitro model in which discrete cellular compartments in a cellularized stromal space are integrated with controlled fluid perfusion elements would be invaluable in understanding better lymphatic biology and pathology of lymphatic disease, as well as modeling more completely the in vivo lymphoid tissue environment in immune response, antibody production, and therapy development efforts.

A need exists for improved models and methods that approximate the complexity of lymphoid tissue structure, function, and dynamics and may be used to gain insight into lymphoid tissue biology and as a model to study disruption thereto for improved therapeutic outcomes.

SUMMARY

The following summary is provided to facilitate an understanding of some of the innovative features unique to the present disclosure and is not intended to be a full description. A full appreciation of the various aspects of the disclosure can be gained by taking the entire specification, claims, drawings, and abstract as a whole.

In one embodiment, a three-dimensional (3D) lymphoid tissue model is provided, comprising: a cellularized stromal compartment comprising one or more stromal cell types in a stromal matrix; a plurality of cellularized compartments comprising lymphocytes, said cellularized compartments disposed within the stromal compartment; and a controlled fluid perfusion system comprising: a fabricated network of microfluidic channels comprising: an inlet channel; an outlet channel; and one or more cross channels, fluidically coupling the inlet channel to the outlet channel, wherein: said microfluidic channels are defined by the stromal matrix after removal of a fugitive material; said network of microfluidic channels is disposed at least partially within the stromal matrix; an inlet port in fluid communication with the network; and an outlet port in fluid communication with the network; wherein said fluid perfusion system is configured to perfuse the lymphoid tissue model with a perfusion fluid.

In another embodiment, a method of fabricating a 3D lymphoid tissue model is provided, the method comprising: casting a network of channels on a polymerized matrix gel with a fugitive material, said network cast to form at least one perfusion inlet channel, at least one perfusion outlet channel, and one or more cross channels; casting pillars of lymphocytes and follicular matrix adjacent to the network of channels to generate a plurality of cellular compartments; incorporating stromal material with one or more stromal cell types to create a stromal matrix; casting the stromal matrix around the cast network of channels and the plurality of cellular compartments; polymerizing the stromal matrix to generate the stromal compartment; flushing the fugitive material from the cast network to yield a network of microfluidic channels; and subjecting the network of microfluidic channels to perfusion with a perfusion fluid.

BRIEF DESCRIPTION OF THE DRAWINGS

The aspects set forth in the drawings are illustrative and exemplary in nature and not intended to limit the subject matter defined by the claims. The following detailed description of the illustrative aspects can be understood when read in conjunction with the following drawings, where like structure is indicated with like reference numerals and in which:

DETAILED DESCRIPTION

Figure 1:
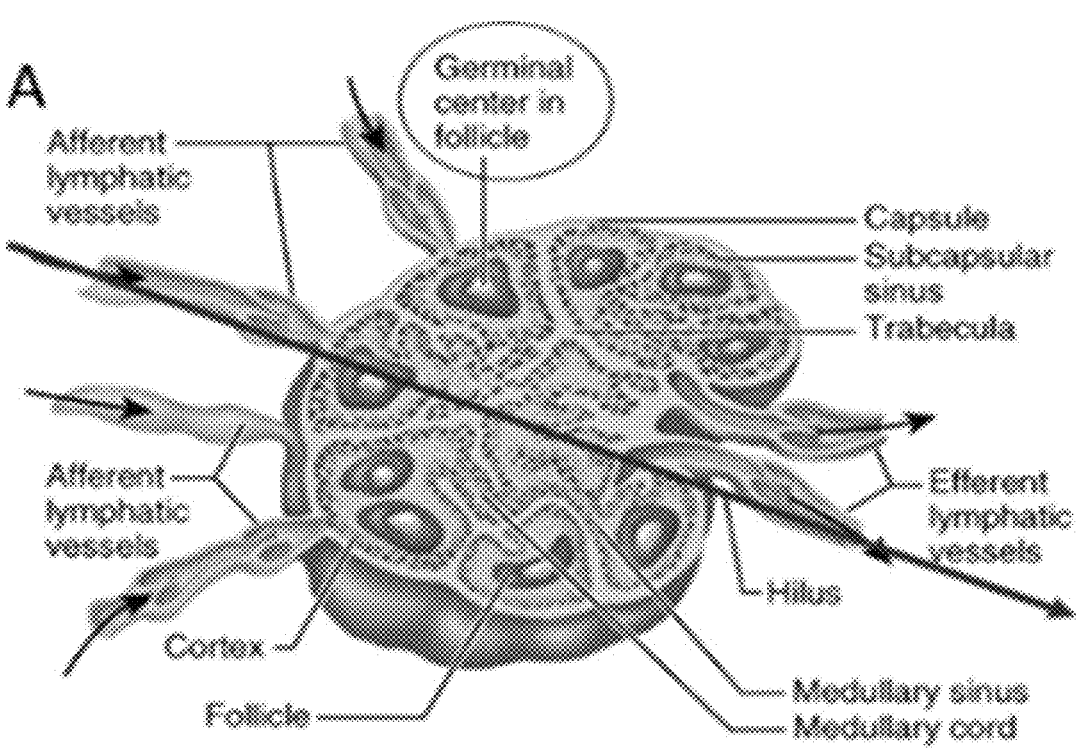
FIG. 1 shows a schematic overview of a human lymph node for understanding and designing embodiments of the present disclosure.

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes or compositions are described as an order of individual steps or using specific materials, it is appreciated that steps or materials may be interchangeable such that the description of the invention may include multiple parts or steps arranged in many ways as is readily appreciated by one of skill in the art.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third" etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, "a first element," "component," "region," "layer," or "section" discussed below could be termed a second (or other) element, component, region, layer, or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Scientific and technical terms used herein are intended to have the meanings commonly understood by those of ordinary skill in the art. Such terms are found defined and used in context in various standard references illustratively including J. Sambrook and D. W. Russell, *Molecular Cloning: A Laboratory Manual*, Cold Spring Harbor Laboratory Press; 3rd Ed., 2001; F. M. Ausubel, Ed., *Short Protocols in Molecular Biology*, Current Protocols; 5th Ed., 2002; B. Alberts et al., *Molecular Biology of the Cell*, 4th Ed., *Garland*, 2002; D. L. Nelson and M. M. Cox, *Lehninger Principles of Biochemistry*, 4th Ed., W.H. Freeman & Company, 2004; Wild, D., *The Immunoassay Handbook*, 3rd Ed., Elsevier Science, 2005; Gosling, J. P., *Immunoassays: A Practical Approach*, Practical Approach Series, Oxford University Press, 2005; *Antibody Engineering*, Kontermann, R. and Dübel, S. (Eds.), Springer, 2001; Harlow, E. and Lane, D., *Antibodies: A Laboratory Manual*, Cold Spring Harbor Laboratory Press, 1988; J. D. Pound (Ed.), *Immunochemical Protocols, Methods in Molecular Biology*, Humana Press; 2nd ed., 1998; B. K. C. Lo (Ed.), *Antibody Engineering: Methods and Protocols, Methods in Molecular Biology*, Humana Press, 2003; and Kohler, G. and Milstein, C., *Nature*, 256:495-497 (1975); the contents of each of which are incorporated herein by reference.

One embodiment is directed to three dimensional (3D) lymphoid tissue models having a cellularized stromal compartment, a plurality of cellularized compartments disposed within the stromal compartment and a controlled fluid perfusion system. The cellularized stromal compartment includes one or more stromal cell types within a stromal matrix. The plurality of cellularized compartments include lymphocytes and/or other immune cells. The controlled fluid perfusion system includes a fabricated network of microfluidic channels having an inlet channel, an outlet channel, and one or more cross channels, fluidically coupling the inlet channel to the outlet channel. The network of microfluidic channels are defined by the polymerization of the stromal matrix, created by the removal of a fugitive material and are disposed at least partially within the stromal matrix. The controlled fluid perfusion system also includes an inlet port and an outlet port in fluid communication with the network of microfluidic channels. The controlled fluid perfusion system is configured to perfuse the stromal compartment with a perfusion fluid.

The mammalian circulatory system includes both the cardiovascular system as well as the lymphatic system. Lymphatic vessels include both macrovessels and microvessels (capillaries), which display significant differences in vessel wall structure. These structural differences also reflect wall compositional differences. While all vessels are lined by a single monolayer of endothelial cells (ECs), the numbers and types of cells comprising the additional layers of the vessel wall vary considerably.

Lymphatic circulation begins in the lymph capillaries. In vivo, intravascular blood plasma is filtered through a semipermeable blood endothelial cell (BEC) layer into extracellular space. The majority of the extravasated interstitial fluid is absorbed by lymphatic capillaries. Lymphatic capillaries have a single layer of lymphatic endothelial cells (LEC) on a permeable basement membrane which direct the flow of interstitial fluid, macromolecules, and immune cells, thereby generating lymph. The lymph is transported to lymphoid tissues, including lymph nodes, via afferent lymphatic vessels, as shown in FIG. 1. The afferent transport of lymph can be directed by chemokine gradients generated by LECs and influenced by interstitial fluid pressure gradients.

Still referring to FIG. 1, after lymph fluid is transported to the lymph node, the lymph is drained into various sinus spaces of the lymph node. These spaces are loosely separated by walls, so lymph fluid flows around them throughout the lymph node. The sinus space of a lymph node is filled with macrophages that engulf foreign particles and pathogens and filter the lymph. The sinuses converge at the hilum of the node, where lymph then leaves the node via an efferent lymphatic vessel toward either a more central lymph node or a lymph duct for drainage into the cardiovascular system.

To mimic the flow of lymph, aspects of the present disclosure include an in vitro lymphoid tissue model 100 having a controlled fluid perfusion system 110. In some aspects, the present disclosure concerns fabricating a network of microfluidic channels 200 to simulate an in vivo circulatory system. This network of microfluidic channels 200 serves as a functional in vitro microcirculation in the lymphoid tissue model 100. In some embodiments, micro-fluidic channels 200 are pre-formed by dispensing a fugitive material into a desired topology in a microfluidic chamber 102, such as a cell-culture well, insert, dish, or other appropriate cell-culture apparatus. Detailed protocols for forming user-defined geometries of perfusable microvessel networks in hydrogel are set forth in Morgan et al. "Formation of microvascular networks in vitro" *Nature Protocols* Vol. 8, No. 9 2013, pp 1820-1836, the entire disclosure of which is incorporated herein by this reference.

The fugitive material is removed once a surrounding matrix, such as the stromal matrix, discussed in further detail below, is applied around the fugitive material, leaving channels forming the network in the surrounding matrix. In some embodiments, the channels are a continuous void within the polymerized medium or matrix such that the polymerized medium or matrix forms the walls of each channel. In some embodiments, the channels may be formed by removal of a solid channel mold after polymerization of the surrounding matrix. In other embodiments, a channel may be formed by inserting a solid-walled structure into liquid medium of the supporting matrix prior to polymerization or completion thereof and withdrawal of the solid walled structure after polymerization. In addition to cast-molding the channels, other techniques may similarly provide a channel, such as by boring.

Figure 2A:
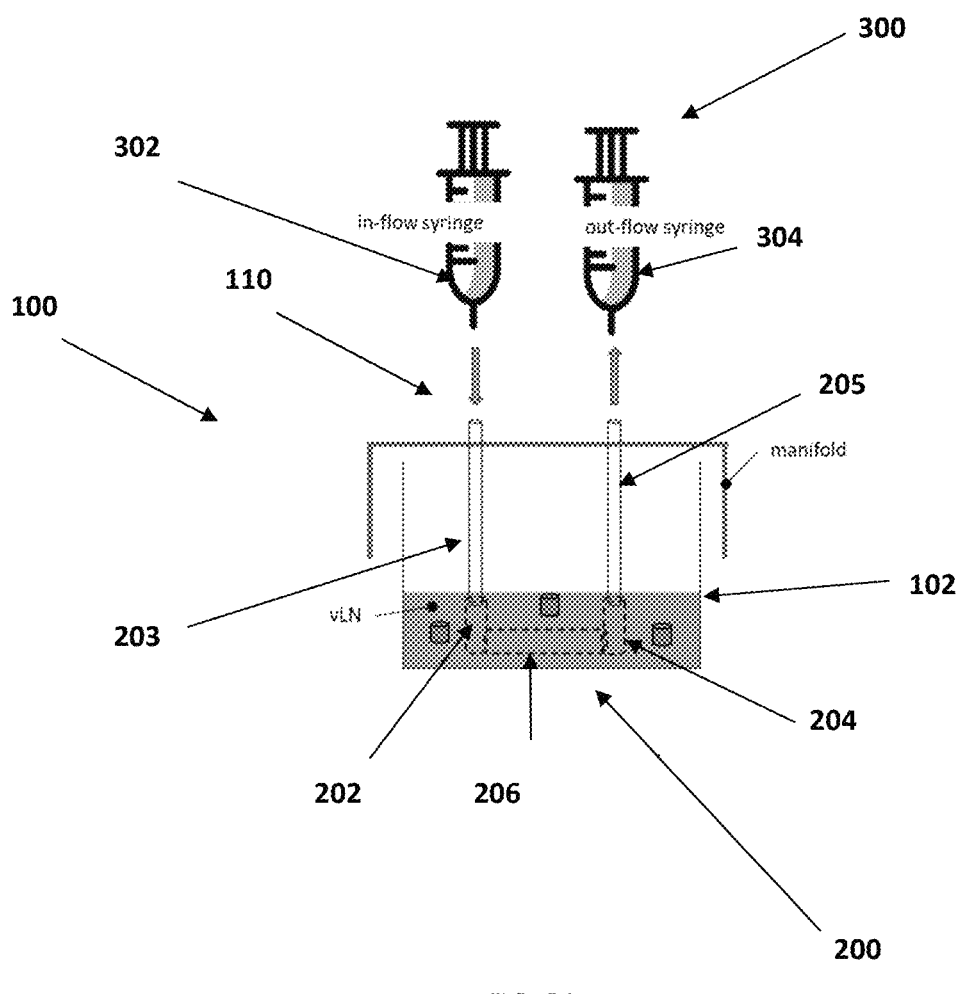
FIG. 2A illustrates a schematic of an illustrative embodiment of the lymphoid tissue model described herein.
Figure 2B:
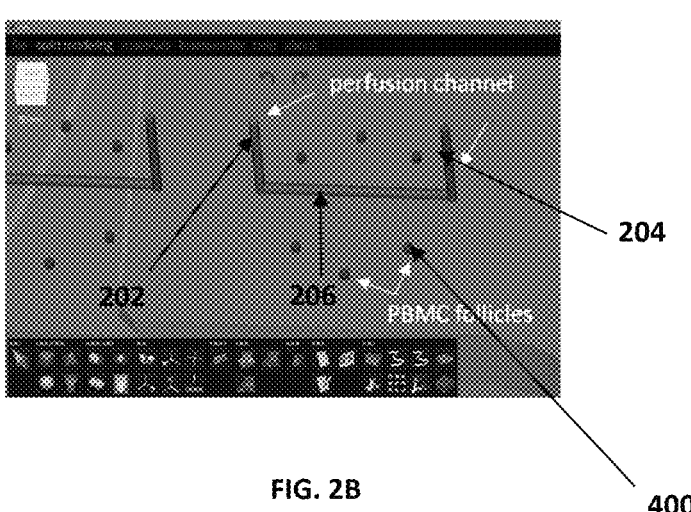
FIG. 2B illustrates a user interface showing tissue structure information modeling (TSIM) software-generated Lymphoid Tissue (LT) Model set up for 3D printing on the BioAssemblyBot® platform.
Figure 2C:
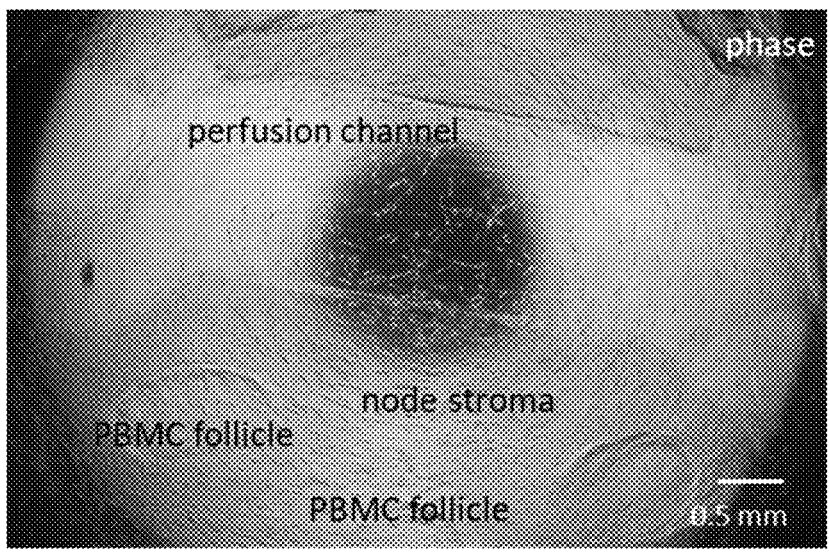
FIG. 2C depicts a top view of a fabricated LT showing different compartments, after incubation and culture for 1 week.
Figure 2D:
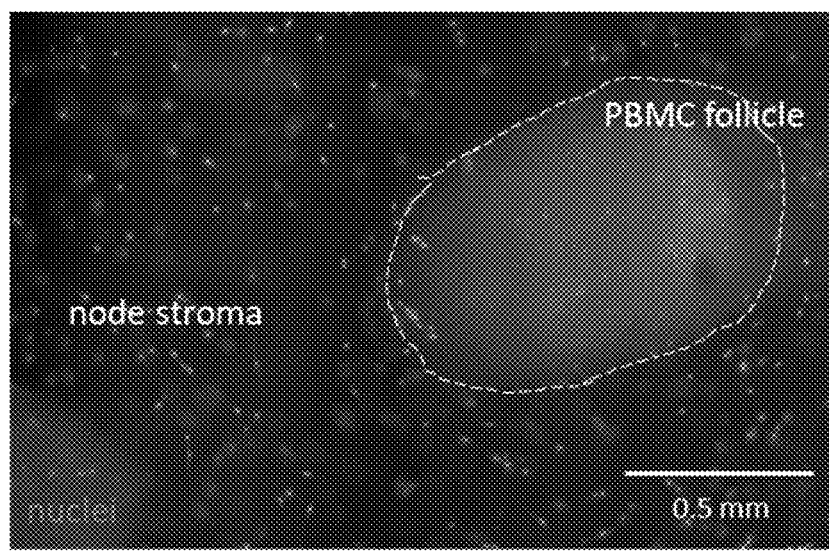
FIG. 2D depicts Hoechst-labelling of fibroblast stroma and PBMC follicle nuclei within the LT model, cultured for one week.

In some embodiments, as depicted in FIGS. 2A, 2B, the fabricated network of microfluidic channels 200 includes an inlet channel 202, an outlet channel 204, and at least one cross channel 206 connecting the inlet channel to the outlet channel, said cross channel 206 disposed at least partially within the surrounding matrix. In embodiments, a plurality of fabricated networks can be disposed within a single microfluidic chamber 102. In embodiments, the fugitive material is a biocompatible hydrogel. In embodiments, the fugitive material includes a thermosensitive poloxamer hydrogel, such as a Pluronic® F127 hydrogel. A range of Pluronic® F127 (poloxamer 407) hydrogels from 10%-30% w/v, including 15%, 20%, 25% and 28% w/v are considered for formation of stiff channel molds.

In some embodiments, such as depicted in FIG. 2B, the network of microfluidic channels 200 is constructed using 3D printing. A sacrificial casting strategy may be employed whereby channel molds comprising a thermoreversible hydrogel or glassing material are 3D printed on the micro-fluidic chamber. BioAssemblyBot® 3-D printing and robotics systems (available from Advanced Solutions Life Sciences, LLC of Louisville, KY) are used to fabricate endothelial cell-lined channels using a fugitive casting approach as a means to connect the network of microfluidic channels 200 to an external perfusion source 300. Methods for fabricating channels via sacrificial casting by exploiting the precision and tolerance benefits and work flow potential of 3-D bioprinting platforms are known. (Miller et al. "Rapid casting of patterned vascular networks for perfusable engineered three-dimensional tissues." *Nature Materials* 11, 768-774 (2012), and Int'l Patent Pub. No. WO2015069619 A1 to Lewis, J. et al.)

In embodiments, the fugitive material is flushed using any acceptable flushing solution, such as Hank's balanced salt solution (HBSS), culture medium, phosphate buffered saline (PBS), and the like. The flushing solution is pushed through one port and out the other as described by others for Pluronic channels in collagen (Hooper et al. *Tissue Eng* Part A. 2014.). In embodiments, after removal of the fugitive material, the patent channels are substantially devoid of material and are defined by the polymerized stromal matrix, discussed in further detail below. In some embodiments, the channel has a diameter or cross-sectional width of between 10 μm and 1000 μm. In some embodiments, each channel has a diameter of about 200 μm.

In embodiments, after the fugitive material is removed, the channels can be seeded with endothelial cells. In embodiments, the endothelial cells are LECs, BECs, or combinations thereof. In embodiments, the channel walls are endothelialized by perfusing a suspension of endothelial cells in media through the channels.

In some embodiments, such as shown in FIG. 2A, the network is connected to an external perfusion system 300, such as a pumping mechanism, using a microfluidic manifold. Non-limiting examples of pumping mechanisms for achieving perfusion include a pressure-driven flow controller, a peristaltic pump, and a syringe mechanism, which may or may not be powered by a motor. In specific embodiments, a CorSolutions™ microfluidics pump is used to provide continuous flow through the chamber with defined flow rates. In embodiments, the perfusion system 300 pressurizes the network of microfluidic channels 200. In embodiments, the inlet channel 202 is connected to an inlet port 203, configured to connect the network to the external perfusion system 300.

In some embodiments, the external perfusion system 300 includes an inlet reservoir 302 or source connected to the network of microfluidic channels 200 such that a perfusion fluid can flow through the channels. In embodiments, the inlet channel 202 is operably connected to the inlet reservoir 302 wherein pressure and/or a pump can cause a fluid media to flow and perfuse the cross channel 206 and exit from the outlet channel 204 and fill into an outlet reservoir 304. In some embodiments, the reservoir 302 is fluidically coupled to the inlet channel 202 via the inlet port 203. In further embodiments, the outlet reservoir 304 is coupled to the outlet channel 204 via an outlet port 205 to collect perfusion fluid. In embodiments, the fluid media is any acceptable cell-culture media for culturing tissue. In some embodiments, discussed in further detail below, the perfusion fluid contains one or more antigens, designed to activate the lymphocytes of the lymphoid tissue model.

In some embodiments, the perfusion system includes a chemokine gradient. Chemokine gradients stimulate directional leukocyte migration and may vary depending on the identity of secreting cells, cell signaling, and other physical parameters. In embodiments, the 3D lymphoid tissue model may be perfused with a solution comprising chemokines, wherein the concentration of chemokines in the perfusion solution differs from the concentration of chemokines in the 3D lymphoid tissue model. When the concentration of chemokines in the perfusion solution differs from the concentration of chemokines in the 3D lymphoid tissue model, a chemokine gradient is established across the perfusion system. Flow rates of the perfusion solution may be adjusted to determine the steepness, or grade of the chemokine gradient.

In some embodiments, the perfusion system is segmented into lymphatic and blood vessel equivalents, modeling fluid movement into, through, and out of the lymphoid tissue, thereby influencing cell dynamics. It will be appreciated that, in vivo, blood supply carries certain populations of cells into and out of the lymphoid tissue. Cells that circulate via the lymphatics differ from cells that circulate through the blood and often contain immune cells, such as antigen presenting cells. Fluid movements within the lymphoid tissue are influenced by both the blood and lymphatic vascular systems. Accordingly, in certain embodiments, the perfusion system comprises lymphatic and blood vessel equivalents that approximate the cell dynamics of in vivo lymphoid tissue.

In some embodiments, over a period of between about 2-7 days, including 3, 4, 5, and 6 days and any range having endpoints defined by any of the aforementioned values, perfusion fluid is perfused into and withdrawn from the inlet reservoir 304 and outlet reservoir 304, respectively that allows the perfusion fluid to traverse the inlet channel to a shared reservoir and then be withdrawn back out via the outlet channel. In some embodiments, the fluid media is perfused at a steady rate. For example, as set forth in the examples herein, the fluid media can be perfused at about 1-100 µl/hr, including about 1, 2, 3, 4, 5, 6, 7, 8, 9, 10, 15, 20, 25, 30, 35, 40, 45, 50, 55, 60, 65, 70, 75, 80, 85, 90, 95, and 100 µl/hr, or any range having endpoints defined by any of the aforementioned values. This allows for in vitro modeling of interstitial flow-conditioning within the lymphoid tissue construct, which will be discussed in greater detail below.

In some embodiments, the outlet can be blocked, for example, by placement of a collagen plug that partially or completely blocks the outlet, or by clipping or collapsing a channel to block fluid flow from the outlet. Such blockage of the outlet creates a backpressure or afterload that influences dynamics so that fluid and cells are circulated within the 3D cell culture as opposed to through a reservoir.

Mammalian lymph nodes contain a large number of B and T lymphocytes, which are transported throughout the node during adaptive immune response. Referring again to FIG. 1, a lymph node is anatomically subdivided into a variety of compartments. Specifically, B cell containing follicles are disposed along the outer cortex of the lymph node. T cells and dendritic cells are disposed within the paracortex. When a lymphocyte is presented with an antigen transported in the lymph, B cells become activated and migrate to the germinal centers of the node, where they proliferate and differentiate to be specific to that antigen.

In some embodiments, the present disclosure concerns generating an in vitro lymphoid tissue model using lymphocytes and the perfusion system, discussed above. In some embodiments, such as depicted in FIGS. 2A-2D, a plurality of cellularized compartments 400 including lymphocytes are disposed adjacent to the network of microfluidic channels in the microfluidic chamber. It will be appreciated that the number of cellularized compartments will vary based on the application of the model, the size of the microfluidic chamber, the length of incubation, and various other considerations known to those skilled in the art. In some embodiments, the number of cellularized compartments ranges from 1 to 50, including 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49, including any range defined by endpoints with the aforementioned values. According to specific embodiments, the plurality of cellularized compartments extend substantially vertically from the microfluidic chamber. "Substantially" herein means within 10% of perpendicular from the base. Other orientations are contemplated depending on analytical or clinical need.

In embodiments, the lymphocytes may be any peripheral blood mononuclear cell (PBMC), including T cells, B cells, or Natural Killer cells, or combinations thereof. In embodiments, the PBMCs are B cells. In some embodiments, additional immune cells (e.g. antigen presenting cells, dendritic cells, monocytes, macrophages, and the like) or components, including but not limited to antigens, cytokines, may be added into the cellularized compartments to allow for the desired cell-cell interactions and/or a closer approximation to a particular lymphoid tissue or organ type.

In embodiments, B cells are isolated or obtained and provided to the lymphoid tissue model. For example, B cells can be excised from a subject and utilized immediately or optionally first treated and/or cultured to remove unwanted extracellular matrix material or tissue and/or enzyme treated, such as with trypsin, to loosen cell-cell associations. In some embodiments, lymphocytes may include established in vitro cell culture cells. In embodiments, B cells can be naïve B cells, memory B cells, or combinations thereof. In some embodiments, B cells can be inactivated or activated (bound to an antigen). In embodiments, the B cells are derived from lymph nodes or lymphoid tissue.

Figure 4:
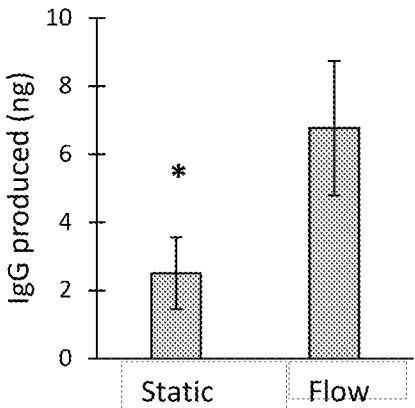
FIG. 4 graphically depicts antibody production using the LT model under static and flow conditions.

In some embodiments, the present disclosure concerns placing lymphocytes in a 3D in vitro culture. In some embodiments, the methods of the present disclosure concern providing a plurality of 3D cellularized compartments comprising lymphocytes to the microfluidic chamber. The methods include casting a plurality of cellularized compartments adjacent to the network of microfluidic channels 200. In some embodiments, the lymphocytes are placed on or embedded within a 3D polymerized medium or matrix. The cellularized compartment is defined by the edges of the polymerized matrix. In embodiments, the matrix includes extracellular matrix proteins and/or structures, including basement membrane proteins and/or basement membrane structures, such as fibrinogen, collagen IV, laminin, nidogen, perlecan sulfated glycolipids, as well as glycoproteins and/or proteoglycans. In some embodiments, the lymphocytes are provided to the perfusion chamber in a dense 3D environment with numerous direct cell-cell and cell-matrix contacts, as they would be in the native tissue environment. In some embodiments, 3D cultures function more effectively than 2D cultures. For example, embodiments of the present disclosure produce greater amounts of antibodies compared with static systems, as shown in FIG. 4 and described in Example 3 below.

In embodiments, the cellularized compartments are fabricated follicles including B cells and a follicular matrix. In embodiments, the follicular matrix includes a hydrogel. The follicular matrix may be selected from a natural hydrogel, a synthetic hydrogel, and hybrid natural and synthetic hydrogels. Non-limiting examples of suitable natural hydrogels include one or more of a collagen, gelatin, fibrin, and a polysaccharide selected from hyaluronic acid (HA), agarose, alginate, and chitosan. Non-limiting examples of suitable synthetic hydrogels include one or more of polydimethylsiloxane (PDMS), polyethylene glycol (PEG), poly(lactic-co-glycolic acid) (PLGA) and polyglycerol sebacate (PGS) polymers. Combinations of natural and synthetic hydrogels are also contemplated. The follicular matrix may also include extracellular matrix proteins and/or structures, including basement membrane proteins and/or basement membrane structures, such as fibrinogen, collagen IV, laminin, nidogen, perlecan sulfated glycolipids, as well as glycoproteins and/or proteoglycans.

In embodiments, the lymphocytes are mixed with the matrix and then allowed to polymerize, generating the cellularized compartment. In some embodiments, the methods of the present disclosure concern preparing lymphocytes prior to introduction into a 3D cell culture system. In some embodiments, the lymphocytes may be pre-cultured to allow the cells therein to adjust to other cell types and/or cell culture conditions and/or media. In some embodiments, the lymphocytes may be pre-treated with antigens. In some embodiments, the cells may be pre-cultured in a 3D matrix prior to use with the perfusion system. In some embodiments, lymphocytes may be co-cultured with microvessels, and then be introduced to the 3D polymerized medium or matrix.

In embodiments, the cellularized compartments are deposited adjacent to the network of microfluidic channels. In embodiments, the cellularized compartments are cast prior to fabricating the network of microfluidic channels. In embodiments, the cellularized compartments are deposited as pillars, though other geometries are contemplated and possible. In embodiments, a plurality of cellularized compartments are added to a single microfluidic chamber. In embodiments, the cellularized compartments are cast by 3D printing the matrix material in the microfluidic chamber. According to specific embodiments, the density of cellular compartments and arrangement in the microfluidic chamber may be varied.

In embodiments, a crosslinking solution is added to the cellularized compartment. In embodiments, the crosslinking solution stabilizes the follicular matrix. In embodiments, the crosslinking solution is added after casting the cellular compartments and subsequently removed after a given time period. In embodiments, the crosslinking solution remains in contact with the cellularized compartment for a period of about 0.25 hrs, 0.5 hrs, 1 hr, 1.5 hrs, 2 hours, or 2.5 hours. In embodiments, the crosslinking solution is removed from the cellularized compartment after 1 hour. In embodiments, the crosslinking solution includes, transglutaminase, and/or thrombin/fibrinogen. In a specific embodiment, fibrinogen is crosslinked with thrombin to form fibrin in the cellularized compartment.

Figure 3A:
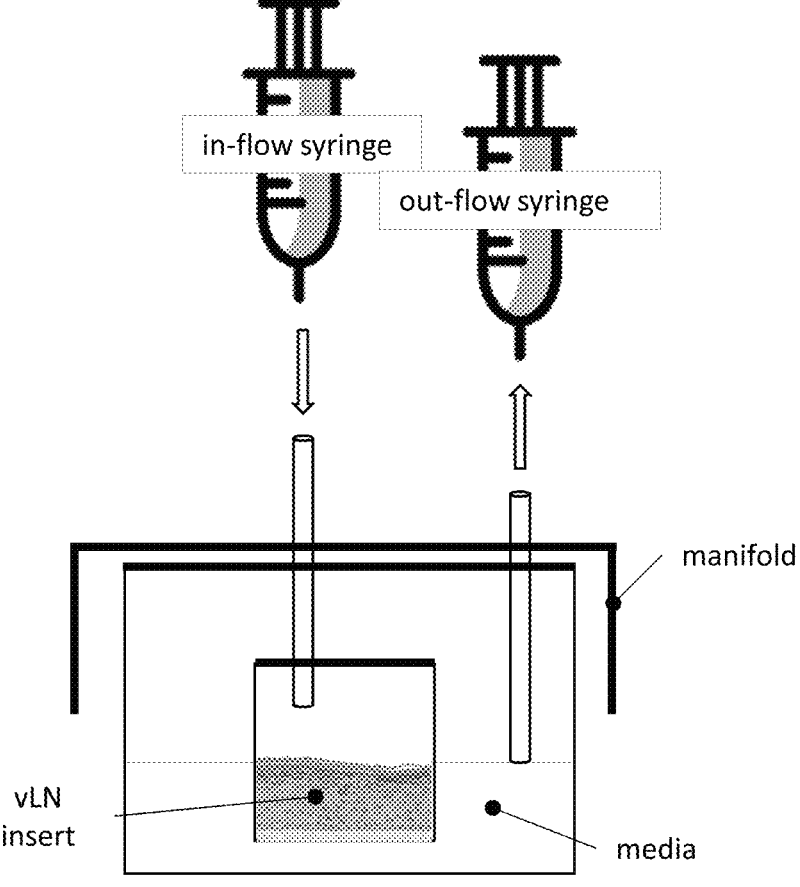
FIG. 3A illustrates a schematic of an illustrative embodiment of the lymphoid tissue model described herein.
Figures 3B, 3C:
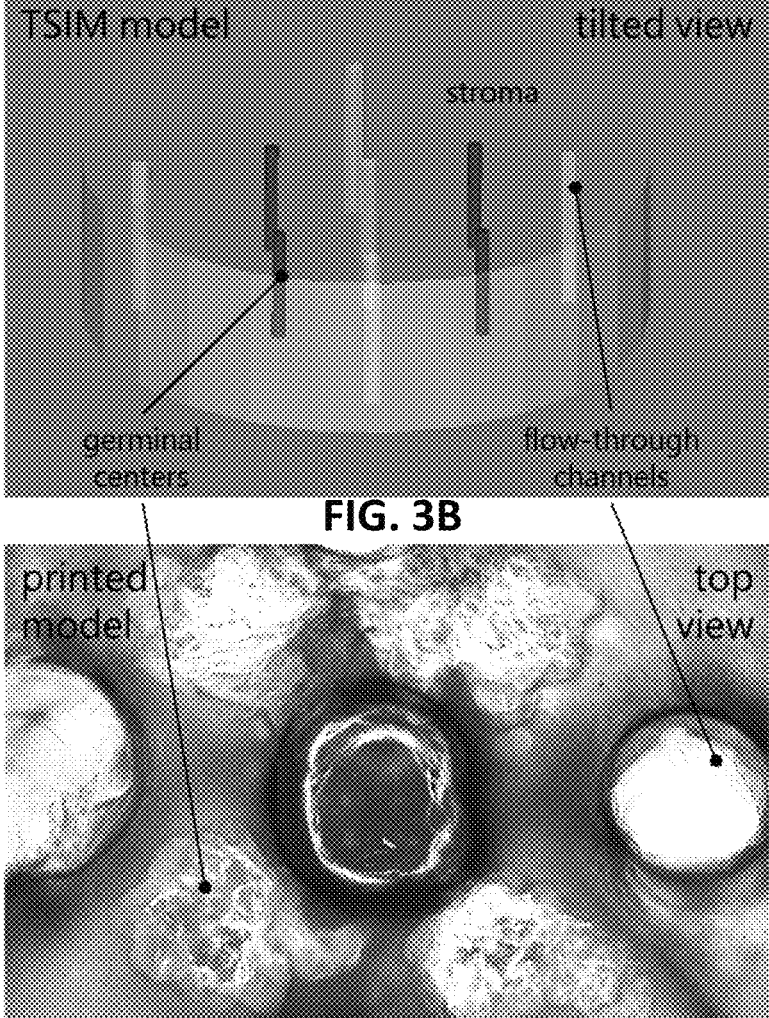
FIG. 3B illustrates a user interface showing tissue structure information modeling (TSIM) software-generated Lymphoid Tissue (LT) Model set up for 3-D printing on the BioAssemblyBot® platform.
FIG. 3C depicts a top view of a fabricated LT showing different compartments, after incubation and culture for 1 week.

In some embodiments, B cells may be pretreated, such as with an antigen, thereby activating the B cells to produce a specific antibody. It will be appreciated that while any antigen may be included or selected, in some embodiments, as the models and methods herein allow, lymphoid tissue models that generate antibodies may in some aspects be particularly useful. According to some embodiments, such as depicted in FIG. 3A, the cellular compartments include activated B cells suspended in the follicular matrix and disposed within the microfluidic chamber, generating a fabricated germinal center. Still referring to FIG. 3A, the network of microfluidic channels can include additional perfusion channels that run substantially vertically to the base of the microfluidic chamber.

In some embodiments, the lymphoid tissue models of the present disclosure include a cellularized stromal compartment. In embodiments, the stromal compartment includes one or more stromal cell types. Stromal cells are a heterogeneous class of cells that play a role during development, tissue injury, regeneration, immune response, cancer, and other pathologies. Stromal cells are differentiating cells that can become connective tissue cells of any organ, such as the uterine mucosa, prostate, bone marrow, lymph node, and ovary. In embodiments, the stromal cell type include mesenchymal stem cells (MSCs). MSCs are stromal cells derived from various sources, such as bone marrow or adipose tissue. MSCs are native cells that may differentiate to a variety of cell types, including osteoblasts, osteocytes. In some embodiments, the stromal cell types are fibroblasts, dendrites, endothelial cells, pericytes, and/or double negative cells or combinations thereof. In some embodiments, the stromal cell type is a fibroblast.

In some embodiments, the stromal cells are suspended within a stromal material to form a stromal matrix. According to specific embodiments, the stromal material comprises any suitable polymerizable gel that sustains biological growth. In embodiments, the stromal matrix is polymerized in the microfluidic chamber. In embodiments, the stromal matrix is cast over the cast network of microfluidic channels and the cellular compartments and polymerized to form a continuous polymerized stromal matrix. In embodiments, the network of microfluidic channels is disposed at least partially within the stromal matrix. In embodiments, the cellular compartments are disposed within the stromal matrix. In embodiments, the stromal material is a collagen solution, a fibrin solution, a Matrigel® solution, a laminin solution, or combinations thereof. In embodiments, polymerization of the solution forms a gel matrix. In some embodiments, the stromal material may include at least one of collagen I, collagen II, collagen III, collagen IV, fibrin, Matrigel® (solubilized basement membrane matrix secreted by Engelbreth-Holm-Swarm mouse sarcoma cells, produced by Corning Life Sciences), laminin, nidogen, perlecan sulfated glycolipids, glycoproteins and/or proteoglycans. In some embodiments, the polymerized stromal matrix may further include additional cell culture co-factors such as albumin, antibiotics, growth factors, cytokines, salts, sodium, potassium, calcium, phosphates, chlorides, and the like.

In some embodiments, the stromal matrix is cast around the network of microfluidic channels and the cellular compartments. In embodiments, the methods comprise 3D printing the stromal matrix around microfluidic channels and the cellular compartments. As noted above, the cellular compartments may be formed by 3D printing. In addition, as discussed above, the microfluidic channels may be formed by printing the channel molds with a fugitive material and removing the fugitive material after the stromal compartment has been cast.

In some embodiments, the lymphoid tissue model further includes pellets of T cells deposited within the stromal matrix. The T cells can be deposited at specific locations and positions relative to the placement of B cell compartments. For example, in embodiments, the pellets or clusters of T cells are disposed at a plurality of locations and/or distances from compartmentalized B cells, thereby approximating the variability of in vivo lymphoid tissue. In embodiments, the pellets of T cells are deposited in a number approximately equal to the number of cellular compartments. In embodiments, the lymphoid tissue model includes more pellets of T cell than cellularized compartments. In embodiments, the lymphoid tissue model includes fewer pellets of T cell than cellularized compartments. In embodiments, the pellets or clusters of T cells are disposed approximately equidistant from the cellularized compartments. In other embodiments, the pellets or clusters of T cells are disposed randomly throughout the stromal compartment.

According to some embodiments, the stromal compartment further comprises a microvasculature. According to specific embodiments, the microvasculature is formed from adding substantially intact native microvessels to the stromal compartment and subjecting the native microvessels to maturing conditions. The present investigators recently disclosed the formation of an adaptable microvasculature in a gel matrix formed from incorporating intact native microvessels into the gel, and subjecting the microvessels to maturing conditions. This is described in detail in U.S. patent application Ser. No. 15/202,675 (the Hoying application), the entire disclosure of which is incorporated herein by this reference. According to very specific embodiments, the intact native microvessels derive from adipose tissue.

Some embodiments of the present invention are directed to methods for manufacturing an in vitro lymphoid tissue model that has cellularized compartments and is capable of facilitating lymphoid tissue cell dynamics, including interstitial fluid flow. According to some embodiments, the methods include: casting a network of channels on a polymerized matrix gel with a fugitive material, said network cast to form at least one perfusion inlet channel, at least one perfusion outlet channel, and one or more cross channels; casting pillars of lymphocytes and follicular matrix substantially adjacent to the network of channels to generate a plurality of cellular compartments; incorporating stromal material with one or more stromal cell types to create a stromal matrix; casting the stromal matrix around the network of microfluidic channels and the cellular compartments; polymerizing the stromal matrix to generate the stromal compartment; flushing the fugitive material from the cast network to yield a network of microfluidic channels; and subjecting the network of microfluidic channels to perfusion with a perfusion fluid.

In some embodiments, the methods also include incubating the lymphoid tissue model under conditions suitable to promote growth of the cells and generation of an immune response. In some embodiments, the methods also include lining the network of microfluidic channels with endothelial cells to form a continuous network of endothelial cell-lined channels. In mores specific embodiments, the methods further comprise adapting the perfusion system to a desired circulatory profile by modulating perfusion of a perfusion fluid through the external perfusion system. system. In specific embodiments, the casting steps may be effectuated by 3D bioprinting.

In some embodiments, the present disclosure concerns methods of generating antibodies utilizing the lymphoid tissue model. In some embodiments, the B cells are activated by an antigen. In specific embodiments, the B cells are activated by incorporation of the antigen into the lymphoid tissue model, such as by incorporation into the perfusion model or the stromal matrix. In other embodiments, B cells are activated prior to incorporation into the lymphoid tissue model. In embodiments, the lymphoid tissue model is perfused, as discussed in detail above, for 2-10 days, including, 3, 4, 5, 6, 7, 8, and 9 days, as well as any range having endpoints defined by any two of the aforementioned values. In embodiments, after incubating for a given time period, the supernatant is collected. In embodiments, antibodies are isolated from the supernatant using any suitable method known, including but not limited to, extraction, precipitation and solubilization, ultracentrifugation and chromatography. In specific embodiments, the antibodies are isolated by one or more of hydrophobic interaction column chromatography, size exclusion chromatography, ion exchange column chromatography, and affinity chromatography. In some embodiments, the isolated antibodies can be purified and administered to a subject in need thereof. In embodiments, a pharmaceutical composition includes the purified antibodies and a pharmaceutically acceptable excipient. In embodiments, the antibodies and/or pharmaceutical compositions are used as a medicine.

Methods for screening therapeutic agents, such as adjuvants, immunosuppressant drugs, immune enhancing drugs, immune checkpoint inhibitors, and the like, for impact on adaptive immune response are also contemplated. According to some embodiments, a control perfusion fluid is formulated for use with the lymphoid tissue models described above. A test perfusion fluid comprising at least one therapeutic agent is also formulated. Lymphoid tissue models according to the above description are perfused with the control perfusion fluid and the test perfusion fluid. The results are compared to determine impact of the agent on the adaptive immune response. A "control" perfusion fluid may not comprise the agent, or may comprise an agent of known impact.

EXAMPLES

Various aspects of the present invention are illustrated by the following non-limiting examples. The examples are for illustrative purposes and are not a limitation on any practice of the present invention. It will be understood that variations and modifications can be made without departing from the spirit and scope of the invention.

Example 1. Production of a 3D Fabricated Lymph
Tissue Model and Assessment of IgG Production The goal of this experiment was to provide a proof of concept for a fabricated 3D lymph node. First, gelatin was mixed with 4 million PBMCs and fibrinogen stock such that final concentrations were 7% gelatin, 1 million/ml cells, and 10 mg/ml fibrinogen. The material was loaded into a 10 cc barrel at 37° C., and allowed a few minutes to cool. A series of 6 dots was printed using a BioAssemblyBot® (Advanced Solutions, Louisville, KY) in each well of a 48 well plate using a 22 GA needle. Then, a crosslinking solution was added to each well, containing 10 mg/ml transglutaminase and 1 U/ml thrombin. Crosslinking prevents the gelatin from dissolving during culture at 37° C. After 1 hour, the crosslinking solution was removed, and a single channel was printed through the middle of each construct with pluronic hydrogel, with inlet and outlet ports on each side. Fibroblasts were resuspended at 200 k/ml in a 3 mg/ml collagen solution and cast over the entire construct. After gelling, several changes of culture medium were used to rinse out remaining pluronic hydrogel. Constructs were then cultured for 5 days in medium containing RPMI, 10% FBS, ITS, 20 ng/ml IL-21, 2.5 µg/ml ODN, 2.5 µg/ml PHA-L, and 15 ng/ml PMA. Supernatants were then removed and concentrated using a protein concentration kit, prior to performing an ELISA for IgG protein. From 15 samples, a total of 6.4 ng of IgG protein was collected.

Example 2. Effects of Interstitial Fluid Flow on
IgG and IgM Production by PBMCs It has also been demonstrated that derivation and expansion of a neovasculature from isolated microvessel fragments in a stromal environment (i.e. made of collagen) in vitro enables rapid (within 24 hrs of transplantation) integration with the host circulation upon implantation. This is true for microvessel fragments derived from mouse, rat, and human. An important aspect of this dynamic is the ability for growing neovessels, as in the body, to locate and inosculate with each other creating a network of immature neovessels that fills the tissue space (FIG. 2). Because this network is interconnected while undergoing active angiogenesis, it can quickly locate and inosculate with an adjacent circulation and begin distributing blood throughout the neovascular work in the implanted graft. This intravascular perfusion then drives development of the fully functioning microcirculation. Interestingly, we have recently shown that stromal cells are important in guiding neovessels across tissue boundaries such as that present between a graft and the implant tissue.

Example 3. Effects of Interstitial Fluid Flow on
PBMC Antibody Production

Peripheral Blood Mononuclear Cells (PBMCs) are a fraction of blood cells that includes lymphocytes (T cells, B cells, NK cells), dendritic cells, and monocytes. These cells play a critical role in the function of the immune system, contributing to both innate and adaptive immunity. When certain lymphocytes within the PBMC fraction become activated in response to an antigen, they produce antibodies. PBMCs are frequently used in assays designed to study and measure immune response, with antibody production being a common metric. These assays have changed little over the years and are relatively simple to perform. Cells are isolated, plated, and activated, either with specific chemical stimuli or other more specific methods. While simple to perform, these assays are limited. In the body, all cells are exposed to low levels of interstitial flow. This flow creates low amounts of shear force on cells, which nearly all cells in the body respond to in one way or another. The purpose of the study was to add interstitial flow to a standard PBMC assay to improve its biological relevance.

Human PBMCs (ATCC) were seeded in the top compartment of polycarbonate membrane cell culture inserts (e.g., "transwells," 0.4 μm pore size) at a density of 1 million per insert. A total of 1.6 ml of culture medium was added to each well. Culture medium contained RPMI supplemented with 10% FBS, 2.5 μg ODN, 2.5 μg PHA-L, 50 ng/ml IL-21, 15 ng/ml PMA, and ITS. The manifold was set up such that one port pumped medium out of the main well, and another added medium to the inside of the cell culture insert, both at a constant rate of 10 μl/hr. This displacement causes medium to constantly flow through the permeable cell culture insert membrane, exposing cells to low levels of shear. Static controls were not exposed to fluid flow.

After 5 days of culture, medium was extracted and used for enzyme-linked immunosorbent assays (ELISA) to compare production of IgG antibodies. Cells exposed to flow produced significantly more IgG than static samples (FIG. 4). While research on the effects of flow on immune cells has been very limited, this study suggests that it may play an important role. Interstitial flow is present in nearly all tissues within the body, thus, including flow will result in a more biomimetic environment.

A first aspect of the present disclosure, either alone or in combination with any other aspect, concerns a three-dimensional (3D) lymphoid tissue model comprising a cellularized stromal compartment comprising one or more stromal cell types in a stromal matrix; a plurality of cellularized compartments comprising lymphocytes, said cellularized compartments disposed within the stromal compartment; and a controlled fluid perfusion system comprising: a fabricated network of microfluidic channels comprising: an inlet channel; an outlet channel; and one or more cross channels, fluidically coupling the inlet channel to the outlet channel, wherein: said microfluidic channels are defined by the stromal matrix after removal of a fugitive material; said network of microfluidic channels is disposed at least partially within the stromal matrix; an inlet port in fluid communication with the network; and an outlet port in fluid communication with the network; wherein said fluid perfusion system is configured to perfuse the lymphoid tissue model with a perfusion fluid.

A second aspect of the present disclosure, either alone or in combination with any other aspect, concerns a 3D lymphoid tissue model wherein the stromal matrix comprises extracellular matrix.

A third aspect of the present disclosure, either alone or in combination with any other aspect, concerns a 3D lymphoid tissue model wherein the extracellular matrix comprises one or more of collagen I, collagen II, collagen III, collagen IV, fibrin, solubilized basement membrane matrix, laminin, nidogen, perlecan, sulfated glycolipids, glycoproteins, hyaluronic acid, and proteoglycans.

A fourth aspect of the present disclosure, either alone or in combination with any other aspect, concerns a 3D lymphoid tissue model wherein the plurality of cellularized compartments comprise B cells and a follicular matrix.

A fifth aspect of the present disclosure, either alone or in combination with any other aspect, concerns a 3D lymphoid tissue model wherein the B cells are activated.

A sixth aspect of the present disclosure, either alone or in combination with any other aspect, concerns a 3D lymphoid tissue model wherein the plurality of cellularized compartments comprise peripheral blood mononuclear cells (PBMC) and a follicular matrix.

A seventh aspect of the present disclosure, either alone or in combination with any other aspect, concerns a 3D lymphoid tissue model wherein the one or more stromal cell types comprise fibroblasts, dendrites, endothelial cells, pericytes, or double negative cells.

An eighth aspect of the present disclosure, either alone or in combination with any other aspect, concerns a 3D lymphoid tissue model wherein the fugitive material comprises a fugitive hydrogel.

A ninth aspect of the present disclosure, either alone or in combination with any other aspect, concerns a 3D lymphoid tissue model wherein the fugitive hydrogel comprises a poloxamer hydrogel.

A tenth aspect of the present disclosure, either alone or in combination with any other aspect, concerns a 3D lymphoid tissue model wherein the stromal compartment further comprises T cell pellets, disposed in the stromal matrix relative to the plurality of cellularized compartments.

An eleventh aspect of the present disclosure, either alone or in combination with any other aspect, concerns a 3D lymphoid tissue model wherein the controlled fluid perfusion system further comprises a perfusion pump.

A twelfth aspect of the present disclosure, either alone or in combination with any other aspect, concerns a 3D lymphoid tissue model, wherein the perfusion fluid further comprises one or more chemokines.

A thirteenth aspect of the present disclosure, either alone or in combination with any other aspect, concerns a 3D lymphoid tissue model wherein the controlled fluid perfusion system is configured to perfuse the perfusion fluid while generating a chemokine gradient.

A fourteenth aspect of the present disclosure, either alone or in combination with any other aspect, concerns a 3D lymphoid tissue model wherein the stromal compartment further comprises microvessels.

A fifteenth aspect of the present disclosure, either alone or in combination with any other aspect, concerns a 3D lymphoid tissue model wherein the network of microfluidic channels are lined with lymphatic endothelial cells, blood endothelial cells, or combinations thereof.

A sixteenth aspect of the present disclosure, either alone or in combination with any other aspect, concerns a method of fabricating a 3D lymphoid tissue model according to any other aspect, the method comprising: casting a network of channels on a polymerized matrix gel with a fugitive material, said network cast to form at least one perfusion inlet channel, at least one perfusion outlet channel, and one or more cross channels; casting pillars of lymphocytes and follicular matrix adjacent to the network of channels to generate a plurality of cellular compartments; incorporating stromal material with one or more stromal cell types to create a stromal matrix; casting the stromal matrix around the cast network of channels and the plurality of cellular compartments; polymerizing the stromal matrix to generate the stromal compartment; flushing the fugitive material from the cast network to yield a network of microfluidic channels; and subjecting the network of microfluidic channels to perfusion with a perfusion fluid.

A seventeenth aspect of the present disclosure, either alone or in combination with any other aspect, concerns a method of fabricating a 3D lymphoid tissue model further comprising depositing cell pellets of T cells within the stromal matrix relative to the cellular compartments.

An eighteenth aspect of the present disclosure, either alone or in combination with any other aspect, concerns a method of producing antibodies with a 3D lymphoid tissue model of any of the previous aspects or a 3D lymphoid tissue model made by any of the previous aspects, 1, the method comprising: activating the lymphocytes by introducing an antigen or an antigen presenting cell; incubating the lymphoid tissue model in the presence of the antigen; collecting a volume of supernatant from the lymphoid tissue model after incubation; isolating the antibodies from the collected supernatant; and purifying the isolated antibodies.

A nineteenth aspect of the present disclosure, either alone or in combination with any other aspect, concerns a method of producing antibodies with a 3D lymphoid tissue model wherein the lymphocytes are B cells and are activated prior to incorporation into the tissue model.

A twentieth aspect of the present disclosure, either alone or in combination with any other aspect, concerns a method of producing antibodies with a 3D lymphoid tissue model wherein the perfusion fluid comprises the antigen.

A twenty-first aspect of the present disclosure, either alone or in combination with any other aspect, concerns a method of producing antibodies with a 3D lymphoid tissue model wherein the perfusion fluid comprises an antigen presenting cell.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified. Methods of nucleotide amplification, cell transfection, and protein expression and purification are similarly within the level of skill in the art.

Patents, publications, and applications mentioned in the specification are indicative of the levels of those skilled in the art to which the invention pertains. These patents, publications, and applications are incorporated herein by reference to the same extent as if each individual patent, publication, or application was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

We claim:

1. A three-dimensional (3D) lymphoid tissue model comprising:
   a cellularized stromal compartment comprising one or more stromal cell types in a stromal matrix;

a plurality of cellularized compartments comprising
   B cells and/or peripheral blood mononuclear cells (PBMC) and a follicular matrix,
   said cellularized compartments disposed within the stromal compartment; and
a controlled fluid perfusion system comprising:
   a fabricated network of microfluidic channels comprising:
      an inlet channel;
      an outlet channel; and
      one or more cross channels, fluidically coupling the inlet channel to the outlet channel,
      wherein:
         said microfluidic channels are defined by the stromal matrix after removal of a fugitive material;
         said network of microfluidic channels is disposed at least partially within the stromal matrix;
         an inlet port in fluid communication with the network; and
         an outlet port in fluid communication with the network;
   wherein said fluid perfusion system is configured to perfuse the lymphoid tissue model with a perfusion fluid.

2. The 3D lymphoid tissue model of claim 1, wherein the stromal matrix comprises extracellular matrix.

3. The 3D lymphoid tissue model of claim 2, wherein the extracellular matrix comprises one or more of collagen I, collagen II, collagen III, collagen IV, fibrin, solubilized basement membrane matrix, laminin, nidogen, perlecan, sulfated glycolipids, glycoproteins, hyaluronic acid, and proteoglycans.

4. The 3D lymphoid tissue model of claim 1, wherein the plurality of cellularized compartments comprise B cells and a follicular matrix.

5. The 3D lymphoid tissue model of claim 4, wherein the B cells are activated.

6. The 3D lymphoid tissue model of claim 1, wherein the plurality of cellularized compartments comprise peripheral blood mononuclear cells (PBMC) and a follicular matrix.

7. The 3D lymphoid tissue model of claim 1, wherein the one or more stromal cell types comprise fibroblasts, dendrites, endothelial cells, pericytes, or double negative cells.

8. The 3D lymphoid tissue model of claim 1, wherein the fugitive material comprises a fugitive hydrogel.

9. The 3D lymphoid tissue model of claim 8, wherein the fugitive hydrogel comprises a poloxamer hydrogel.

10. The 3D lymphoid tissue model of claim 1, wherein the stromal compartment further comprises T cell pellets, disposed in the stromal matrix relative to the plurality of cellularized compartments.

11. The 3D lymphoid tissue model of claim 1, wherein the controlled fluid perfusion system further comprises a perfusion pump.

12. The 3D lymphoid tissue model of claim 1, wherein the perfusion fluid further comprises one or more chemokines.

13. The 3D lymphoid tissue model of claim 12, wherein the controlled fluid perfusion system is configured to perfuse the perfusion fluid while generating a chemokine gradient.

14. The 3D lymphoid tissue model of claim 1, wherein the stromal compartment further comprises microvessels.

15. The 3D lymphoid tissue model of claim 1, wherein the network of microfluidic channels are lined with lymphatic endothelial cells, blood endothelial cells, or combinations thereof.

16. A method of fabricating a 3D lymphoid tissue model, the method comprising:

casting a network of channels on a polymerized matrix gel with a fugitive material, said network cast to form at least one perfusion inlet channel, at least one perfusion outlet channel, and one or more cross channels;

casting pillars of lymphocytes and follicular matrix adjacent to the network of channels to generate a plurality of cellular compartments;

incorporating stromal material with one or more stromal cell types to create a stromal matrix;

casting the stromal matrix around the cast network of channels and the plurality of cellular compartments;

polymerizing the stromal matrix to generate the stromal compartment;

flushing the fugitive material from the cast network to yield a network of microfluidic channels; and subjecting the network of microfluidic channels to perfusion with a perfusion fluid.

17. The method according to claim 16, further comprising depositing cell pellets of T cells within the stromal matrix relative to the plurality of cellular compartments.

18. A method of producing antibodies with the 3D lymphoid tissue model of claim 1, the method comprising:

activating the lymphocytes by introducing an antigen or an antigen presenting cell;

incubating the lymphoid tissue model in the presence of the antigen;

collecting a volume of supernatant from the lymphoid tissue model after incubation;

isolating the antibodies from the collected supernatant; and purifying the isolated antibodies.

19. The method according to claim 18, wherein the lymphocytes are B cells and are activated prior to incorporation into the tissue model.

20. The method according to claim 18, wherein the perfusion fluid comprises the antigen.

21. The method according to claim 18, wherein the perfusion fluid comprises an antigen presenting cell.

* * * * *